United States Patent
Bhalavi et al.

(10) Patent No.: US 10,702,795 B2
(45) Date of Patent: Jul. 7, 2020

(54) PROCESS FOR HIGH PURITY HEXANE AND PRODUCTION THEREOF

(71) Applicant: Indian Oil Corporation Limited, Bandra (East), Mumbai (IN)

(72) Inventors: Prakash Bhagwant Bhalavi, Faridabad (IN); Irudayaraj Devotta, Faridabad (IN); Naduhatty Selai Raman, Faridabad (IN); Brijesh Kumar, Faridabad (IN); Biswapriya Das, Faridabad (IN)

(73) Assignee: INDIAN OIL CORPORATION LIMITED, Mumbai (IN)

( * ) Notice: Subject to any disclaimer, the term of this patent is extended or adjusted under 35 U.S.C. 154(b) by 501 days.

(21) Appl. No.: 15/409,218

(22) Filed: Jan. 18, 2017

(65) Prior Publication Data

US 2017/0203231 A1  Jul. 20, 2017

(30) Foreign Application Priority Data

Jan. 18, 2016  (IN) .............................. 201621001722

(51) Int. Cl.
| | |
|---|---|
| *B01D 3/40* | (2006.01) |
| *C07C 7/08* | (2006.01) |
| *B01D 3/14* | (2006.01) |
| *B01D 5/00* | (2006.01) |
| *C07C 7/09* | (2006.01) |
| *C07C 7/00* | (2006.01) |

(52) U.S. Cl.
CPC ............. *B01D 3/40* (2013.01); *B01D 3/143* (2013.01); *B01D 5/0063* (2013.01); *C07C 7/005* (2013.01); *C07C 7/08* (2013.01); *C07C 7/09* (2013.01)

(58) Field of Classification Search
None
See application file for complete search history.

(56) References Cited

U.S. PATENT DOCUMENTS

| | | | |
|---|---|---|---|
| 2,728,800 A | 12/1955 | Manne et al. | |
| 2,847,485 A | 8/1958 | Van Dyck Fear | |
| 2,856,444 A | 10/1958 | Pollock | |
| 3,505,421 A | 4/1970 | Lumbroso et al. | |

(Continued)

FOREIGN PATENT DOCUMENTS

| | | |
|---|---|---|
| IN | 189165 | 12/2002 |
| IN | 189517 | 3/2003 |

OTHER PUBLICATIONS

Sigma-Aldrich, n-hexane grades (Year: 2019).*
Solis Oil, Naphtha, Heavy Naphtha, and Light Naphtha (Year: 2019).*

*Primary Examiner* — Derek N Mueller
(74) *Attorney, Agent, or Firm* — Workman Nydegger (57) ABSTRACT

The invention relates to the production of High purity n-hexane from low value stream such as raffinate from benzene extraction unit in crude oil refineries employing extractive distillation. The present invention further related to an extractive distillation employing an organic solvent having comparable or same Hansen dispersive force parameter ($\delta_d$) of that of the key component of to be separated through extractive distillation. The present invention is useful for separating and isolating pure cyclohexane, pure methylcyclopentane and pure iso-heptane along with the pure n-hexane.

10 Claims, 1 Drawing Sheet

(56) References Cited

U.S. PATENT DOCUMENTS

| | | | |
|---|---|---|---|
| 3,551,327 A | | 12/1970 | Kelly et al. |
| 3,942,765 A | | 3/1976 | Henrickson |
| 3,963,934 A | | 6/1976 | Ormrod |
| 4,278,505 A | * | 7/1981 | Danulat .............. C07C 7/005 203/58 |
| 4,314,974 A | | 2/1982 | Libby et al. |
| 4,428,829 A | | 1/1984 | Kosters |
| 4,567,315 A | | 1/1986 | Owaysi et al. |
| 5,254,763 A | | 10/1993 | Gill et al. |
| 5,294,334 A | | 3/1994 | Kaul et al. |
| 5,460,700 A | * | 10/1995 | Berg .................... C07C 7/08 203/60 |
| 5,668,293 A | | 9/1997 | Forestiere et al. |
| 6,048,450 A | | 4/2000 | Mikitenko et al. |
| 6,153,805 A | | 11/2000 | Jose |
| 7,501,549 B2 | | 3/2009 | Podrebarac et al. |
| 2002/0024395 A1 | | 2/2002 | Akatsuka et al. |
| 2004/0182750 A1 | | 9/2004 | Khanna et al. |
| 2005/0224395 A1 | | 10/2005 | Manna et al. |
| 2014/0353216 A1 | | 12/2014 | Scibola et al. |

\* cited by examiner

PROCESS FOR HIGH PURITY HEXANE AND PRODUCTION THEREOF

FIELD OF THE INVENTION

The invention relates to the production of High purity hexane from low value stream such as raffinate from benzene extraction unit in crude oil refineries employing extractive distillation.

BACKGROUND OF THE INVENTION

The naphtha solvents have different applications in chemical and petrochemical industries such as solvents for extraction of vegetable oil, polymerization process and for cleanup and maintenance operations. Naphtha solvents used in food processing to extract selective ingredient from a raw material, should follow the criteria set for toxicological norms and in petrochemical process. High purity hexane is naphtha solvent in the range of 65° C. to 70° C. with aromatics, mainly benzene known as High purity hexane widely used in polymerization and food industry.

Several processes such as catalytic hydrogenation, adsorptive de-aromatization, catalytic distillation and solvent extraction have been currently followed in industry for reduction of benzene in naphtha for the production of food grade hexane.

U.S. Pat. No. 3,505,421 describes a process of hydrogenating benzene in liquid phase by means of molecular hydrogen in the presence of suspended solid catalyst. U.S. Pat. No. 5,254,763 also describes a process for selective hydrogenation of benzene using water soluble organo-metallic hydrogenation catalyst. This hydrogenation process involves hydrogen at elevated temperature and pressure. The hydrogenation process also involves the removal of sulfur before the reaction, which makes this process more expensive.

The adsorptive de-aromatization was achieved using activated carbon, alumina, and zeolite materials. U.S. Pat. No. 3,963,934 claims the separation of aromatics from process streams by use of a molecular sieve. Other U.S. Pat. Nos. 2,728,800; 2,847,485; and 2,856,444 describes the use of silica gel for adsorbing aromatics from a process stream, followed by desorption by use of a liquid hydrocarbon. U.S. Pat. No. 5,294,334 describes the process for selectively removing benzene from gasoline boiling range process streams using aluminosilicate zeolite material. The catalytic distillation for benzene removal is another method/technology.

U.S. Pat. No. 7,501,549 claims the reduction in benzene from gasoline can be achieved by feeding a gasoline fraction with an alcohol and ether to a catalytic distillation column with one reaction zone containing an alkylation catalyst. Then the $C_6$ hydrocarbons are separated from $C_{7+}$ hydrocarbons. The catalytic hydrogenation is another method for benzene removal where benzene reduction, olefin saturation and sulfur reduction occurs simultaneously.

U.S. Pat. No. 6,153,805 discloses the catalytic hydrogenation of benzene to produce cyclohexane in the presence of metal catalyst. US Patent Application 2002/24395 discloses the production of food grade hexane by hydrogenation, using Ni supported alumina catalyst. U.S. Pat. No. 4,428,829 reports the production of food grade hexane by separating aromatics and non-aromatics from heavy hydrocarbon stream by extraction process.

U.S. Pat. No. 5,668,293 discloses the process and catalyst for the production of cyclohexane by hydrogenation of benzene, comprising of two steps: a) gradually introducing the feed of benzene for hydrogenation and a hydrogen-rich gas into a reaction zone containing a cyclohexane-rich liquid and a nickel-based catalyst in colloidal suspension and recovering a gaseous phase containing cyclohexane, hydrogen and benzene; and b) introducing the gaseous phase into a reactor operating under hydrogenation conditions and containing at least one fixed bed of a solid nickel-based hydrogenation catalyst.

Indian patent applications 1224/DEL/1994 & 788/DEL/1994 discloses the separation of the aromatics and non-aromatics from naphtha and kerosene range fraction by extraction. The raffinate phase is water washed to remove the solvent carryover. The U.S. patent application 20040182750 discloses the process for removal of aromatics from petroleum streams like naphtha, kerosene and gasoil through extraction by using solvents like NMP, Sulfolane and glycol. In all the above said process, solvent is recovered by distillation.

U.S. Pat. No. 3,551,327 discloses a process for recovery of aromatics from vapour to liquid phase i.e. by extractive distillation, further it also focuses on raffinate water wash and recovery of sulfolane from water. US patent application 20040182750 discloses a process for extraction of aromatics from petroleum fraction like heavy naphtha, kerosene and gas oil. U.S. Pat. Nos. 3,942,765; 4,314,974 discloses a process for the removal of metal ions from aqueous solution by using solvent in different type of static mixer and then whole process is confined to static mixer alone. The processes for producing food grade hexane containing less than 100 ppm benzene is hydrogenation (U.S. patent application 20050224395) and adsorption (U.S. Pat. No. 4,567,315).

U.S. Pat. No. 6,048,450 discloses a process for the selective reduction in the content of light unsaturated compounds (that is to say containing at the most six carbon atoms per molecule) including benzene, in a hydrocarbon cut comprising mainly at least 5 carbon atoms per molecule, without any significant loss in the octane number, said process comprising passing said cut into a distillation zone associated with a hydrogenation reaction zone, followed by passing part of the effluent from the distillation zone comprising mainly $C_5$-$C_6$ hydrocarbons, that is to say containing 5 and/or 6 carbon atoms per molecule into a zone for the isomerization of paraffins in the presence of an isomerization catalyst, to obtain an isomerate containing an increased concentration of branched hydrocarbons.

US20140353216 discloses a column for consecutive extractive distillations, in particular of crude hydrocarbon mixes comprising aromatic, naphthene and paraffin hydrocarbons. It also discloses the methods for separating and recovering the components of a crude hydrocarbon mix comprising aromatic, naphthene and paraffin hydrocarbons by consecutive extractive distillations.

All the above discussed prior arts need the refineries, which are producing food grade hexane by solvent extraction process, need to put up separate unit to employ these processes which is cost intensive.

Specifications for food grade hexane with respect to benzene content are becoming stringent day by day. Refineries producing food grade hexane by solvent extraction process need to switch to alternative processes like catalytic hydrogenation and adsorption which calls for additional capital investment. Thus there is a need for a process for production of High purity hexane employing extractive distillation using solvent having similar dispersive force parameter to that of component.

OBJECTIVES OF THE INVENTION

It is an object of this invention to provide a process for production of High purity hexane.

It is another objective of this invention to provide pure cyclohexane, methylcyclopentane and iso-heptane.

It is another objective of invention of separating n-hexane (also referred as hexane) from other paraffins by extractive distillation employing an organic solvent having comparable or same Hansen dispersive force as that of n-hexane.

SUMMARY OF THE INVENTION

The present invention relates to a process of preparing high purity n-hexane by extractive distillation of a hydrocarbon feedstock, wherein the extractive distillation is carried out using an organic solvent having comparable to same Hansen dispersive force parameter ($\delta_d$) to hexane.

The present invention further relates to a process for producing pure n-hexane, said process comprising:
(a) subjecting a benzene saturated hydrocarbon stream to fractional separation at a temperature in range of 65° C. to 100° C. to split the benzene saturated hydrocarbon stream into a bottom stream comprising a mixture of cyclohexane and iso-heptane and a top stream comprising a mixture of methylcyclopentane (MCP) and n-hexane;
(b) subjecting the top stream of step (a) to extractive distillation to obtain n-hexane and methylcyclopentane by using an organic solvent; and
(c) separating pure n-hexane.

The present invention further relates to an apparatus for producing pure n-hexane, said apparatus comprising:
(a) a fractional distillation unit [4] to split a benzene saturated hydrocarbon stream into a bottom stream comprising cyclohexane and iso-heptane, and a top stream comprising methylcyclopentane (MCP) and n-hexane;
(b) an extractive distillation column [8] for fractionating the top stream into an overhead stream rich in n-hexane and a bottom stream comprising methylcyclopentane and organic solvent;
(c) a solvent storage [29] for introducing solvent to the extractive distillation column [8];
(d) a condenser [31] for condensing pure n-hexane stream wherein a portion of condensed stream is passed to the extractive distillation column [8] through a conduit [17]; and
(e) a conduit [21] for isolating pure n-hexane.

DESCRIPTION OF THE INVENTION

While the invention is susceptible to various modifications and/or alternative processes and/or compositions, specific embodiment thereof has been shown by way of example in the drawings and tables and will be described in detail below. It should be understood, however that it is not intended to limit the invention to the particular processes and/or compositions disclosed, but on the contrary, the invention is to cover all modifications, equivalents, and alternative falling within the spirit and the scope of the invention as defined by the appended claims.

The tables have been represented where appropriate by conventional representations showing only those specific details that are pertinent to understanding the embodiments of the present invention so as not to obscure the disclosure with details that will be readily apparent to those of ordinary skill in the art having benefit of the description herein.

The following description is of exemplary embodiments only and is not intended to limit the scope, applicability or configuration of the invention in any way. Rather, the following description provides a convenient illustration for implementing exemplary embodiments of the invention. Various changes to the described embodiments may be made in the function and arrangement of the elements described without departing from the scope of the invention.

In accordance with this invention, in a process for the simultaneous production of cyclohexane, methylcyclopentane and high purity hexane from $C_6$ refinery stream containing 6-7 carbon atoms by employing series of processes including fractional distillation, and extractive distillation using a solvent (also referred to as extractant or entrainer) in extractive distillation unit wherein said solvent is at least one saturated alcohol selected from the group consisting of alkanols and cycloalkanols, wherein said alkanols are selected from the group comprising of C5 to C9 carbon atoms.

Accordingly, the main embodiment of the present invention relates to a process of preparing high purity n-hexane by extractive distillation of a hydrocarbon feedstock, wherein the extractive distillation is carried out using an organic solvent having comparable to same Hansen dispersive force parameter ($\delta_d$) to hexane.

In other embodiment the hydrocarbon feedstock is a light naphtha feedstock comprising $C_6$ raffinate stream of paraffins and cycloparaffins.

In a preferred embodiment the hydrocarbon feedstock is mixture of predominately cyclohexane, methylcyclopentane, n-hexane and iso-heptanes.

In another embodiment, the organic solvent is selected from the group comprising of C5-C9 alkanols and C5-C9 cycloalkanols.

In another preferred embodiment, the organic solvent is selected from monoethylene glycol (MEG), triethylene glycol (TEG), N-methyl pyrrolidone (NMP), Sulfolane and dimethyl sulfoxide (DMSO). In most preferred embodiment, the organic solvent is selected from monoethylene glycol (MEG) and triethylene glycol (TEG) with matching Hansen solubility parameter and more preferably the matching dispersive force.

Hansen Solubility Parameter:

Solvents suitable for extractive distillation of compounds of interest were selected based on Hansen solubility parameter in the present invention. When a compound is dissolved in a solvent, intermolecular interactions develop between molecules, in order to achieve good solubility, intermolecular interaction force between the solute and solvent should be identical or at least comparable. When the non-polar molecules dissolves in the polar solvent, stronger intermolecular force develop than those in non-polar solutes. The solubility characteristics of the solvent and solute are based on three parameters which are known as the Hansen Solubility Parameters. The Hansen Solubility Parameters are the factors that determine which set of molecules will interact strongly with other molecules. The stronger the interaction, the more soluble those compounds are expected to be. Hence it is an effective method at determining ideal solvents for given solutions of feed. These three forces are:

1) Energy from dispersion force between molecules ($\delta_d$)
2) Energy from dipolar inter-molecular forces between molecules ($\delta_p$)
3) Energy from Hydrogen-bonding between molecules ($\delta_h$).

In Table-1, only cyclohexane and MCP have equal dispersion force (8.2 & 7.7 respectively) as that of solvents, MEG and TEG (8.3 & 7.8 respectively) which is a dominant force for measuring/ensuring good solubility compared to dipolar intermolecular force and hydrogen bonding. The other solvent like NMP and sulfolane do not give the required separation for the High purity hexane because they have higher dispersion force than TEG.

TABLE 1

| Substance | dispersion force ($\delta_d$) | dipolar inter-molecular force ($\delta_p$) | Hydrogen-bonding ($\delta_p$) |
|---|---|---|---|
| MEG | 8.3 | 5.4 | 12.7 |
| TEG | 7.8 | 6.1 | 9.1 |
| NMP | 8.8 | 6.0 | 3.5 |
| SULFOLANE | 9 | 7.4 | 5.3 |
| DMSO | 9 | 8 | 5 |
| Cyclohexane | 8.2 | 0.0 | 0.1 |
| Methylcyclopentane | 7.7 | 1.7 | 0.0 |
| Hexane | 7.3 | 0.0 | 0.0 |
| 2,4-Dimethylpentane | 7 | 0 | 0 |

In another preferred embodiment, solvent preferred based on the matching Hansen dispersive force enhances separation factor.

In another preferred embodiment, the enhanced separation factor improves purity of preferred components namely cyclohexane as well as methylcyclopentane and thus reduces separation stages.

The present invention is a process for producing high purity hexane as well as cyclohexane and methylcyclopentane from light naphtha feedstock. The feed of $C_6$ raffinate stream contains paraffin and cycloparaffins. Benzene saturated hydrocarbon stream is fed to fractional distillation to separate the mixture of cyclohexane and heptanes at the bottom of the column and mixture of methylcyclopentane and n-hexane at the top of the column. Then the both streams processes through extractive distillation separately. In an extractive distillation column, solvent is added which separates the components by changing the relative volatilities of the components of the mixture and effective separation by distillation becomes possible. The solvent for extractive distillation is chosen on the basis of solubility and comparable Hansen dispersive force as that of component to be separated to cause great differences between the relative volatilities of the components in a mixture and ease the separation with fewer distillation stages, lower amount of reflux and higher product purity.

Accordingly, in another preferred embodiment, the present invention provides a process for producing pure n-hexane, said process comprising:
(a) subjecting a benzene saturated hydrocarbon stream to fractional separation at a temperature in range of 65° C. to 100° C. to split the benzene saturated hydrocarbon stream into a bottom stream comprising a mixture of cyclohexane and iso-heptane and a top stream comprising a mixture of methylcyclopentane (MCP) and n-hexane;
(b) subjecting the top stream of step (a) to extractive distillation to obtain n-hexane and methylcyclopentane by using an organic solvent; and
(c) separating pure n-hexane.

In other embodiment, after benzene saturation, the hydrocarbon feed (i.e. saturated light naphtha feedstock) contains predominantly cyclohexane, methylcyclopentane and paraffins like n-hexane and iso-heptanes with benzene less <100 ppm. The minimum boiling point of feed should not be less than 65 and should not be more than 100.

In another embodiment, the extractive distillation of top stream further comprises of:
(a) subjecting a feed containing top stream comprising methylcyclopentane and n-hexane to the extractive distillation;
(b) separating n-hexane rich stream and methylcyclopentane rich stream from the feed of step (a) by addition of an organic solvent wherein the solvent to the feed ratio is 3% vol/vol;
(c) isolating the n-hexane rich stream and a methylcyclopentane rich stream containing organic solvent separately;
(d) partially condensing the n-hexane rich stream of step (c) to obtain pure n-hexane; and
(e) separating the organic solvent from the methylcyclopentane rich stream of step (c) to obtain pure methylcyclopentane.

In one another embodiment, a portion of condensed stream of n-hexane obtained from step (d) is returned back as a reflux for the extractive distillation.

In one another embodiment, the organic solvent obtained from step (e) is recycled back to step (b) for separation of the n-hexane rich stream and methylcyclopentane rich stream from the feed.

In a preferred embodiment, the organic solvent is selected from monoethylene glycol (MEG), triethylene glycol (N-methyl pyrrolidone (NMP), sulfolane and dimethyl sulfoxide (DMSO) and most preferably from MEG and TEG.

In another embodiment, the extractive distillation of the bottom stream of step (b) comprises steps of:
(a) subjecting a feed containing bottom stream comprising a mixture of cyclohexane and iso-heptane to extractive distillation;
(b) separating iso-heptane rich stream and cyclohexane rich stream from the feed of step (a) by addition of an organic solvent wherein the solvent to the feed ratio is 3% vol/vol;
(c) isolating the iso-heptane rich stream and a cyclohexane rich stream containing organic solvent separately;
(d) partially condensing the iso-heptane rich stream of step (c) to obtain pure iso-heptane; and
(e) separating the organic solvent from the cyclohexane rich stream of step (c) to obtain pure cyclohexane.

In further embodiment, a portion of condensed stream of iso-heptane obtained from step (d) is returned back as a reflux for the extractive distillation.

Also, the organic solvent obtained from step (e) is recycled back to step (b) for separation of the iso-heptane rich stream and cyclohexane rich stream from the feed.

Figure 1:
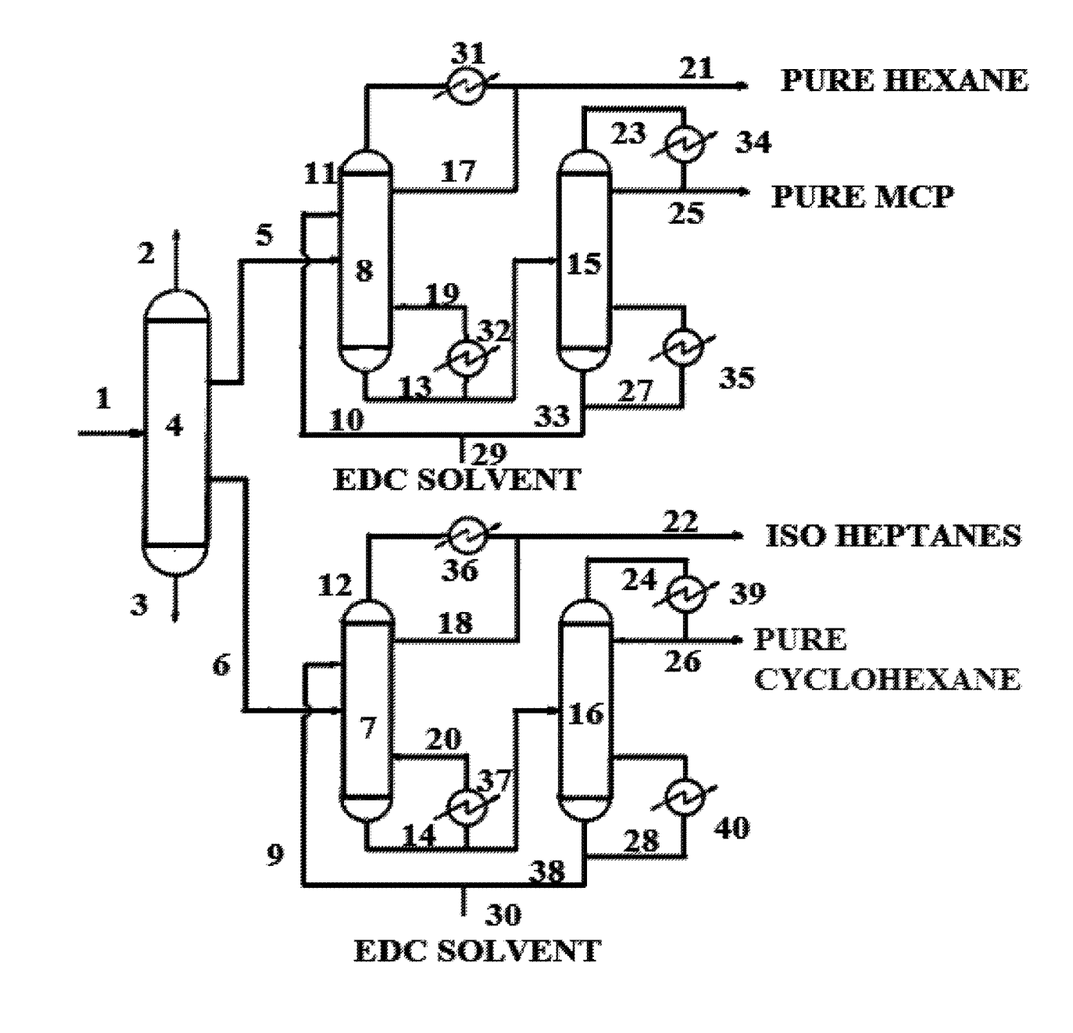
FIG. 1 is a diagrammatic representation of apparatus for producing pure n-hexane, pure methylcyclopentane, pure cyclohexane and pure iso-heptane.

The feed mixture comprising $C_6$ raffinate hydrocarbons and para-xylene raffinate is benzene saturated where benzene is converted into cyclohexane. The benzene saturated hydrocarbon stream thus obtained is sent to fractionators [4] through conduit [1] for splitting into two streams to cyclohexane rich bottom stream through conduit [6] and MCP rich stream through conduit [5] respectively. The lighter fractions [2] (having hydrocarbon with carbon atoms less than $C_6$) and the heavier fractions [3] (having hydrocarbon with carbon atoms more than $C_6$) are separated from the fractionator [4].

Extractive Distillation:

The MCP rich stream containing n-hexane conduit [5] is then fed to extractive distillation column [8] where the Solvent from solvent storage [29] is introduced to extractive distillation column [8] through conduit [10], and an overhead stream enriched in High purity hexane is withdrawn from an upper portion of distillation column [8] through conduit [11]. This overhead stream can be partially condensed, with a portion thereof being returned to the fractionation zone as reflux. The overhead stream passing through conduit [11] is condensed in condenser [31] to yield a condensed overhead stream. A portion of the condensed overhead stream can be returned to distillation column [8] as reflux through conduit [17], while the remainder of the condensed overhead stream is yielded as a High purity hexane through conduit [21].

A bottoms stream of extractive distillation column [8] rich with MCP is withdrawn from a lower portion of the extractive distillation column [8] through conduit [13]. A portion of the fluids withdrawn from the bottom of extractive distillation column [8] may be heated in reboiler [32] and then passed back to a lower portion of extractive distillation column [8] through conduit [19]. The feed mixture introduced into extractive distillation column [8] will be fractionated to yield an overhead stream which is enriched in High purity hexane and a bottoms stream predominantly comprising the MCP and the solvent.

The bottoms stream passing through conduit [13] is passed to distillation column [15]. Differences in the boiling point and adjustment of the temperature in the distillation column, the bottoms stream passing through conduit [13] can be easily fractionated into solvent stream [33]. An overhead stream predominantly comprising MCP is withdrawn from an upper portion of distillation column [15] through conduit [23]. This overhead stream can be at least partially condensed in condenser [34]. A portion of the overhead stream withdrawn from condenser [34] can be returned through conduit [25] as reflux for MCP through conduit [25].

A bottoms stream mainly comprising the solvent is withdrawn from a lower portion of distillation column [15] through conduit [33]. A portion of this bottoms stream is preferably routed back to solvent stream [29] and then recycled to extractive distillation column [8], while another portion of the bottoms stream is heated in a reboiler [35] and returned to the lower portion of column [15]. Solvent lost during processing is made up by a makeup stream passing through conduit [33] and solvent stream [29].

The cyclohexane rich stream conduit [6] is then fed to extractive distillation column [7] where the Solvent from solvent storage [30] is introduced to extractive distillation column [7] through conduit [9], and an overhead stream enriched in iso-heptanes is withdrawn from an upper portion of distillation column [7] through conduit [12]. This overhead stream can be partially, with a portion thereof being returned to the fractionation zone as reflux. The overhead stream passing through conduit [12] is condensed in condenser [36] to yield a condensed overhead stream. A portion of the condensed overhead stream can be returned to distillation column [7] as reflux through conduit [18], while the remainder of the condensed overhead stream is yielded as a product through conduit [22].

A bottom stream of extractive distillation column [7] rich with cyclohexane is withdrawn from a lower portion of the extractive distillation column [7] through conduit [14]. A portion of the fluids withdrawn from the bottom of distillation column [14] may be heated in reboiler [37] and then passed back to a lower portion of distillation column [7] through conduit [20].

The feed mixture introduced into extractive distillation column [7] will be fractionated to yield an overhead stream which is enriched in High purity hexane and a bottoms stream predominantly comprising the cyclohexane and the solvent.

The bottom stream passing through conduit [14] is passed to distillation column [16]. Differences in the boiling point and adjustment of the temperature in the distillation column, the bottoms stream passing through conduit [14] can be easily fractionated into solvent stream [38]. An overhead stream predominantly comprising cyclohexane is withdrawn from an upper portion of distillation column [16] through conduit [24]. This overhead stream can be at least partially condensed in condenser [39]. A portion of the overhead stream withdrawn from condenser [39] can be returned through conduit [26] as reflux for distillation column [16], with the remainder of the overhead stream being withdrawn as product, i.e., cyclohexane through conduit [26].

A bottom stream predominantly comprising the solvent is withdrawn from a lower portion of distillation column [16] through conduit [38]. A portion of this bottoms stream is preferably routed back to solvent stream [30] and then recycled to extractive distillation column [7], while another portion of the bottoms stream is heated in a reboiler [40] and returned to the lower portion of column [16]. Solvent lost during processing losses can be made up by a makeup stream passing through conduit [38] and solvent stream [30].

Accordingly, in another embodiment, the present invention relates to an apparatus for producing pure n-hexane wherein said apparatus comprising:
  (a) a fractional distillation unit [4] to split a benzene saturated hydrocarbon stream into a bottom stream comprising cyclohexane and iso-heptane, and a top stream comprising methylcyclopentane (MCP) and n-hexane;
  (b) an extractive distillation column [8] for fractionating the top stream into an overhead stream rich in n-hexane and a bottom stream comprising methylcyclopentane and organic solvent;
  (c) a solvent storage [29] for introducing solvent to the extractive distillation column [8];
  (d) a condenser [31] for condensing pure n-hexane stream wherein a portion of condensed stream is passed to the extractive distillation column [8] through a conduit [17]; and
  (e) a conduit [21] for isolating pure n-hexane.

In another embodiment of the present invention, the apparatus of the present invention further comprises of:
  (a) a distillation column [15] for separating pure methylcyclopentane stream and organic solvent;
  (b) a condenser [34] for condensing the pure methylcyclopentane stream wherein a portion of condensed methylcyclopentane stream is returned to the distillation column [15] as a reflux through conduit [25] and remaining is isolated through conduit [25];
  (c) a conduit [33] for transferring a portion of organic solvent from the distillation column [15] to the solvent storage [29]; and (d) a reboiler [35] for heating a portion of the organic solvent and returning the hot organic solvent to the bottom of the distillation column [15].

In one another embodiment, the apparatus of the present invention further comprises of:
(a) an extractive distillation column [7] for fractionating overhead iso-heptane rich stream and a bottom stream comprising cyclohexane and organic solvent;
(b) a solvent storage [30] for introducing solvent to the extractive distillation column [7];
(c) a condenser [36] for condensing the overhead iso-heptane stream wherein a portion of condensed stream is returned to the extractive distillation column [7] as a reflux through a conduit [18];
(d) a conduit [22] for isolating pure iso-heptane.

In one another embodiment of the present invention, the apparatus of the present invention further comprises of:
(a) a distillation column [16] for fractionating cyclohexane and organic solvent wherein isolating pure cyclohexane stream from top of the distillation column [16] and organic solvent from bottom of the distillation column [16];
(b) a condenser [39] for condensing the pure cyclohexane stream wherein a portion of condensed cyclohexane stream is returned to the distillation column [16] through conduit [26] and remaining is isolated through conduit [26];
(c) a conduit [38] for transferring a portion of organic solvent from the distillation column [16] to the solvent storage [30]; and
(d) a reboiler [40] for heating a portion of the organic solvent and returning the hot organic solvent to the bottom of the distillation column [16].

In further embodiment, the process of the present invention optionally comprises of a step wherein a portion of the fluids withdrawn from the bottom of the extractive distillation column [8] may be heated in reboiler [32] and then passed back to a lower portion of extractive distillation column [8] through conduit [19].

Example 1

Experiments were conducted with hydrocarbon feedstock consisting of hexane and methylcyclopentane with MEG as a solvent. The solvent-to feed ratio was 3 vol/vol. The mixture of solvent and feed were heated to a temperature of 75° C. and the vapors were condensed and completely refluxed back to the solvent feed mixture. After 2 hours of distillation and total reflux, samples of both liquid and condensed vapor were collected and analyzed for composition. The results are summarized in the following table.

|  | Feed | Liquid Phase | Vapor Phase |
| --- | --- | --- | --- |
| n-Hexane % | 69.1 | 58.23 | 72.41 |
| Methylcyclopentane, % | 30.9 | 41.77 | 27.59 |

The separation factor in the above example has been found to be 1.88

Example 2

Experiments were conducted with hydrocarbon feedstock consisting of hexane and methyl cyclopentane with TEG as a solvent. The solvent-to feed ratio was 3 vol/vol. The mixture of solvent and feed were heated to a temperature of 75° C. and the vapors were condensed and completely refluxed back to the solvent feed mixture. After 2 hours of distillation and total reflux, samples of both liquid and condensed vapor were collected and analyzed for composition. The results are summarized in the following table.

|  | Feed | Liquid Phase | Vapor Phase |
| --- | --- | --- | --- |
| n-Hexane % | 87.91 | 93.61 | 86.48 |
| Methylcyclopentane, % | 12.09 | 6.93 | 13.51 |

The separation factor in the above example has been found to be 2.29

Example 3

Experiments were conducted with hydrocarbon feedstock consisting of hexane and methyl cyclopentane with NMP as a solvent. The solvent-to feed ratio was 3 vol/vol. The mixture of solvent and feed were heated to a temperature of 75° C. and the vapors were condensed and completely refluxed back to the solvent feed mixture. After 2 hours of distillation and total reflux, samples of both liquid and condensed vapor were collected and analyzed for composition. The results are summarized in the following table.

|  | Feed | Liquid Phase | Vapor Phase |
| --- | --- | --- | --- |
| n-Hexane % | 90.51 | 89.78 | 97.10 |
| Methylcyclopentane, % | 9.49 | 10.22 | 2.90 |

The separation factor in the above example has been found to be 3.81

Example 4

Experiments were conducted with hydrocarbon feedstock consisting of hexane and methyl cyclopentane with Sulfolane as a solvent. The solvent-to feed ratio was 3 vol/vol. The mixture of solvent and feed were heated to a temperature of 75° C. and the vapors were condensed and completely refluxed back to the solvent feed mixture. After 2 hours of distillation and total reflux, samples of both liquid and condensed vapor were collected and analyzed for composition. The results are summarized in the following table:

|  | Feed | Liquid Phase | Vapor Phase |
| --- | --- | --- | --- |
| n-Hexane % | 89.56 | 89.10 | 91.70 |
| Methylcyclopentane, % | 10.44 | 10.90 | 8.30 |

The separation factor in the above example has been found to be 1.35

Example 5

Experiments were conducted with hydrocarbon feedstock consisting of hexane and methyl cyclopentane with DMSO as a solvent. The solvent-to feed ratio was 3 vol/vol. The mixture of solvent and feed were heated to a temperature of 75° C. and the vapors were condensed and completely refluxed back to the solvent feed mixture. After 2 hours of distillation and total reflux, samples of both liquid and condensed vapor were collected and analyzed for composition. The results are summarized in the following table.

|  | Feed | Liquid Phase | Vapor Phase |
|---|---|---|---|
| n-Hexane % | 89.02 | 89.77 | 90.05 |
| Methylcyclopentane, % | 10.18 | 10.23 | 9.95 |

The separation factor in the above example has been found to be 1.03

Example 6

Experiments were conducted with hydrocarbon feedstock consisting of hexane and methyl cyclopentane with MEG as a solvent. The solvent-to feed ratio was 3 vol/vol. The mixture of solvent and feed were heated to a temperature of 75° C. and the vapors were condensed and completely refluxed back to the solvent feed mixture. After 2 hours of distillation and total reflux, samples of both liquid and condensed vapor were collected and analyzed for composition. The results are summarized in the following table.

|  | Feed | Liquid Phase | Vapor Phase |
|---|---|---|---|
| Methylcyclopentane, % | 98.24 | 99.57 | 97.78 |
| n-Hexane, % | 1.73 | 0.43 | 2.22 |

The separation factor in the above example has been found to be 5.25

Example 7

Experiments were conducted with hydrocarbon feedstock consisting of hexane and methyl cyclopentane with NMP as a solvent. The solvent-to feed ratio was 3 vol/vol. The mixture of solvent and feed were heated to a temperature of 75° C. and the vapors were condensed and completely refluxed back to the solvent feed mixture. After 2 hours of distillation and total reflux, samples of both liquid and condensed vapor were collected and analyzed for composition. The results are summarized in the following table.

|  | Feed | Liquid Phase | Vapor Phase |
|---|---|---|---|
| Methylcyclopentane, % | 0.74 | 0.82 | 0.37 |
| n-Hexane, % | 99.26 | 99.18 | 99.63 |

The separation factor in the above example has been found to be 2.22

Example 8

Experiments were conducted with hydrocarbon feedstock consisting of hexane and methyl cyclopentane with NMP as a solvent. The solvent-to feed ratio was 3 vol/vol. The mixture of solvent and feed were heated to a temperature of 75° C. and the vapors were condensed and completely refluxed back to the solvent feed mixture. After 2 hours of distillation and total reflux, samples of both liquid and condensed vapor were collected and analyzed for composition. The results are summarized in the following table.

|  | Feed | Liquid Phase | Vapor Phase |
|---|---|---|---|
| Methylcyclopentane, % | 90.45 | 91.35 | 82.81 |
| n-Hexane, % | 9.55 | 8.65 | 17.19 |

The separation factor in the above example has been found to be 2.19

Example 9

Experiments were conducted with hydrocarbon feedstock consisting of hexane and methyl cyclopentane with Sulfolane as a solvent. The solvent-to feed ratio was 3 vol/vol. The mixture of solvent and feed were heated to a temperature of 75° C. and the vapors were condensed and completely refluxed back to the solvent feed mixture. After 2 hours of distillation and total reflux, samples of both liquid and condensed vapor were collected and analyzed for composition. The results are summarized in the following table.

|  | Feed | Liquid Phase | Vapor Phase |
|---|---|---|---|
| Methylcyclopentane, % | 89.03 | 88.55 | 91.27 |
| n-Hexane, % | 10.97 | 11.44 | 8.73 |

The separation factor in the above example has been found to be 0.74

Example 10

Experiments were conducted with hydrocarbon feedstock consisting of hexane and methyl cyclopentane with DMSO as a solvent. The solvent-to feed ratio was 3 vol/vol. The mixture of solvent and feed were heated to a temperature of 75° C. and the vapors were condensed and completely refluxed back to the solvent feed mixture. After 2 hours of distillation and total reflux, samples of both liquid and condensed vapor were collected and analyzed for composition. The results are summarized in the following table.

|  | Feed | Liquid Phase | Vapor Phase |
|---|---|---|---|
| Methylcyclopentane, % | 87.54 | 86.81 | 91.04 |
| n-Hexane, % | 12.45 | 13.19 | 12.45 |

The separation factor in the above example has been found to be 0.647

The data summarized in Table II indicates that for separation of hexane from MCP for the production of high purity n-hexane, MEG, TEG and NMP acts as a better solvent compare to DMSO and Sulfolane.

TABLE II

| SOLVENT | FEED (%) | | LIQUID FRACTION (%) | | VAPOR FRACTION (%) | | S/F | Sep Factor |
|---|---|---|---|---|---|---|---|---|
| | MCP | HEXANE | MCP | HEXANE | MCP | HEXANE | | |
| MEG | 69.1 | 30.9 | 58.23 | 41.77 | 72.41 | 27.59 | 3 | 1.88 |
| TEG | 12.09 | 87.91 | 6.93 | 93.61 | 13.51 | 86.48 | 3 | 2.29 |
| NMP | 9.49 | 90.51 | 10.21 | 89.79 | 2.89 | 97.10 | 3 | 3.81 |
| SULFOLANE | 10.44 | 89.56 | 10.89 | 89.10 | 8.30 | 91.70 | 3 | 1.35 |
| DMSO | 10.18 | 89.02 | 10.23 | 89.77 | 9.94 | 90.05 | 3 | 1.03 |
| MEG | 98.24 | 1.73 | 99.57 | 0.43 | 97.78 | 2.22 | 3 | 5.25 |
| NMP | 0.74 | 99.26 | 0.82 | 99.18 | 0.37 | 99.63 | 3 | 2.22 |
| NMP | 90.45 | 9.55 | 91.35 | 8.65 | 82.81 | 17.19 | 3 | 2.19 |
| SULFOLANE | 89.03 | 10.97 | 88.55 | 11.44 | 91.27 | 8.73 | 3 | 0.74 |
| DMSO | 87.54 | 12.45 | 86.81 | 13.19 | 91.04 | 8.96 | 3 | 0.64 |

*S/F is solvent to feed ratio

Example 11

Experiments were conducted with hydrocarbon feedstock consisting of cyclohexane and iso-heptane with MEG as a solvent. The solvent-to feed ratio was 3 vol/vol. The mixture of solvent and feed were heated to a temperature of 80° C. and the vapors were condensed and completely refluxed back to the solvent feed mixture. After 2 hours of distillation and total reflux, samples of both liquid and condensed vapor were collected and analyzed for composition. The results are summarized in the following table.

| | Feed | Liquid Phase | Vapor Phase |
|---|---|---|---|
| Cyclohexane | 84.59 | 85.87 | 83.97 |
| Iso-heptanes | 15.41 | 14.13 | 16.03 |

The separation factor in the above example has been found to be 1.16

Example 12

Experiments were conducted with hydrocarbon feedstock consisting of cyclohexane and iso-heptanes with MEG as a solvent. The solvent-to feed ratio was 3 vol/vol. The mixture of solvent and feed were heated to a temperature of 80° C. and the vapors were condensed and completely refluxed back to the solvent feed mixture. After 2 hours of distillation and total reflux, samples of both liquid and condensed vapor were collected and analyzed for composition. The results are summarized in the following table.

| | Feed | Liquid Phase | Vapor Phase |
|---|---|---|---|
| Cyclohexane | 98.98 | 99.3 | 98.35 |
| Iso-heptanes | 1.02 | 0.7 | 1.65 |

The separation factor in the above example has been found to be 2.37.

Example 13

Experiments were conducted with hydrocarbon feedstock consisting of cyclohexane and iso-heptanes with NMP as a solvent. The solvent-to feed ratio was 3 vol/vol. The mixture of solvent and feed were heated to a temperature of 80° C. and the vapors were condensed and completely refluxed back to the solvent feed mixture. After 2 hours of distillation and total reflux, samples of both liquid and condensed vapor were collected and analyzed for composition. The results are summarized in the following table.

| | Feed | Liquid Phase | Vapor Phase |
|---|---|---|---|
| Cyclohexane | 90.09 | 90.41 | 87.28 |
| Iso-heptanes | 9.91 | 9.59 | 12.72 |

The separation factor in the above example has been found to be 1.37.

Example 14

Experiments were conducted with hydrocarbon feedstock consisting of cyclohexane and iso-heptanes with NMP as a solvent. The solvent-to feed ratio was 3 vol/vol. The mixture of solvent and feed were heated to a temperature of 80° C. and the vapors were condensed and completely refluxed back to the solvent feed mixture. After 2 hours of distillation and total reflux, samples of both liquid and condensed vapor were collected and analyzed for composition. The results are summarized in the following table.

| | Feed | Liquid Phase | Vapor Phase |
|---|---|---|---|
| Cyclohexane | 97.17 | 99.32 | 98.48 |
| Iso-heptanes | 0.83 | 0.67 | 1.51 |

The separation factor in the above example has been found to be 2.25.

Example 15

Experiments were conducted with hydrocarbon feedstock consisting of cyclohexane and iso-heptanes with DMSO as a solvent. The solvent-to feed ratio was 3 vol/vol. The mixture of solvent and feed were heated to a temperature of 80° C. and the vapors were condensed and completely refluxed back to the solvent feed mixture. After 2 hours of distillation and total reflux, samples of both liquid and condensed vapor were collected and analyzed for composition. The results are summarized in the following table.

|  | Feed | Liquid Phase | Vapor Phase |
|---|---|---|---|
| Cyclohexane | 90.45 | 90.69 | 89.29 |
| Iso-heptanes | 9.55 | 9.30 | 10.71 |

The separation factor in the above example has been found to be 1.17.

Example 16

Experiments were conducted with hydrocarbon feedstock consisting of cyclohexane and iso-heptanes with Sulfolane as a solvent. The solvent-to feed ratio was 3 vol/vol. The mixture of solvent and feed were heated to a temperature of 80° C. and the vapors were condensed and completely refluxed back to the solvent feed mixture. After 2 hours of distillation and total reflux, samples of both liquid and condensed vapor were collected and analyzed for composition. The results are summarized in the following table.

|  | Feed | Liquid Phase | Vapor Phase |
|---|---|---|---|
| Cyclohexane | 89.50 | 89.67 | 87.77 |
| Iso-heptanes | 10.59 | 10.33 | 12.22 |

The separation factor in the above example has been found to be 0.826.

The data summarized in Table III indicates that for separation of Cyclohexane from iso-heptane, MEG, TEG and NMP are better solvent compare to DMSO and Sulfolane

TABLE III

| SOLVENT | FEED (%) | | LIQUID FRACTION (%) | | VAPOR FRACTION (%) | | S/F | Sep Factor |
|---|---|---|---|---|---|---|---|---|
|  | Chex | i-hep | Chex | i-hep | Chex | i-hep |  |  |
| MEG | 84.59 | 15.41 | 85.87 | 14.13 | 83.97 | 16.03 | 3 | 1.16 |
| TEG | 98.98 | 1.02 | 99.3 | 0.7 | 98.35 | 1.65 | 3 | 2.37 |
| NMP | 90.09 | 9.91 | 90.41 | 9.59 | 87.28 | 12.72 | 3 | 1.37 |
| NMP | 99.17 | 0.83 | 99.32 | 0.68 | 98.48 | 1.51 | 3 | 2.25 |
| SULFOLANE | 89.50 | 10.59 | 89.67 | 10.33 | 87.77 | 12.22 | 3 | 0.826 |
| DMSO | 90.45 | 9.55 | 90.69 | 9.31 | 89.29 | 10.71 | 3 | 1.17 |

Simulation studies were also carried out with Aspen to simulate the flow scheme given in FIG. 1. Studies were done to determine the number of theoretical stage that are required in each column of extractive distillation and recovery of solvent and recycle. The result indicated that the cyclohexane is recovered at the bottom of column [8] along with the solvent and solvent free iso-heptane at the top of same column. Methylcyclopentane with solvent and solvent free High purity n-hexane (also referred as hexane) is also recovered at the bottom and top of column [7] respectively. The simulation also confirmed that the solvent can be recovered and recycled. After solvent recovery, solvent free cyclohexane and methylcyclopentane are recovered in column [16] and [15] respectively. The simulation results were in line with the experimental data and validated the experiment findings.

Accordingly, the present invention relates to a process which is useful for isolation of pure methylcyclopentane, pure iso-heptane and pure cyclohexane along with the pure n-hexane.

The invention claimed is:

1. A process for producing n-hexane, said process comprising:
   (a) subjecting a benzene saturated hydrocarbon stream to fractional separation at a temperature in range of 65° C. to 100° C. to split the benzene saturated hydrocarbon stream into a top stream and a bottom stream, wherein the bottom stream comprises a mixture of cyclohexane and iso-heptane and the top stream comprises a mixture of methylcyclopentane (MCP) and n-hexane;
   (b) subjecting the top stream of step (a) to extractive distillation to obtain n-hexane and methylcyclopentane by using an organic solvent; and
   (c) separating n-hexane.

2. The process as claimed in claim 1, wherein the extractive distillation of said top stream of step (a) further comprises steps of:
   (a) subjecting a feed containing the top steam comprising methylcyclopentane and n-hexane to the extractive distillation;
   (b) separating a n-hexane rich stream and a methylcyclopentane rich stream from the feed of step (a) by addition of an organic solvent wherein the solvent to the feed ratio is 3% vol/vol;
   (c) isolating the n-hexane rich stream and the methylcyclopentane rich stream containing organic solvent separately;
   (d) partially condensing the n-hexane rich stream of step (c) to obtain a condensed stream comprising n-hexane; and
   (e) separating the organic solvent from the methyl cyclopentane rich stream of step (c) to obtain methylcyclopentane.

3. The process as claimed in claim 2, wherein a portion of the condensed stream of n-hexane obtained from step (d) is returned back as a reflux for the extractive distillation.

4. The process as claimed in claim 2, wherein the organic solvent obtained from step (e) is recycled back to step (b) for separation of the n-hexane rich stream and methylcyclopentane rich stream from the feed.

5. The process as claimed in claim 2, wherein the organic solvent is selected from monoethylene glycol (MEG), triethylene glycol (TEG), N-methyl pyrrolidone (NMP), sulfolane and dimethyl sulfoxide (DMSO).

6. The process as claimed in claim 1, wherein the extractive distillation of the bottom stream of step (b) comprises steps of:
   (a) subjecting a feed containing the bottom stream comprising a mixture of cyclohexane and iso-heptane to extractive distillation;
   (b) separating an iso-heptane rich stream and a cyclohexane rich stream from the feed of step (a) by addition of an organic solvent wherein the solvent to the feed ratio is 3% vol/vol;
   (c) isolating the iso-heptane rich stream and the cyclohexane rich stream containing organic solvent separately;
   (d) partially condensing the iso-heptane rich stream of step (c) to obtain isoheptane; and
   (e) separating the organic solvent from the cyclohexane rich stream of step (c) to obtain cyclohexane.

7. The process as claimed in claim 6, wherein a portion of condensed stream of iso-heptane obtained from step (d) is returned back as a reflux for the extractive distillation.

8. The process as claimed in claim 6, wherein the organic solvent is selected from monoethylene glycol (MEG), triethylene glycol (TEG), N-methyl pyrrolidone (NMP), sulfolane and dimethyl sulfoxide (DMSO).

9. The process as claimed in claim 6, wherein the organic solvent obtained from step (e) is recycled back to step (b) for separation of the iso-heptane rich stream and cyclohexane rich stream from the feed.

10. The process as claimed in claim 1, wherein the process is further used for isolation of methylcyclopentane, iso-heptane and cyclohexane along with the n-hexane.

* * * * *